United States Patent [19]

Murugesan

[11] Patent Number: 5,420,123
[45] Date of Patent: May 30, 1995

[54] DIBENZODIAZEPINE ENDOTHELIN ANTAGONISTS

[75] Inventor: Natesan Murugesan, Lawrenceville, N.J.

[73] Assignee: Bristol-Myers Squibb Company, Princeton, N.J.

[21] Appl. No.: 993,562

[22] Filed: Dec. 21, 1992

[51] Int. Cl.$^6$ .................. C07D 487/04; A61K 31/55
[52] U.S. Cl. ..................... 514/220; 540/495
[58] Field of Search ................ 540/495; 514/220

[56] References Cited

U.S. PATENT DOCUMENTS

| | | | |
|---|---|---|---|
| 4,415,496 | 11/1983 | Harris et al. | 260/239.3 B |
| 4,661,479 | 4/1987 | Wyvratt, Jr. et al. | 514/214 |
| 4,724,236 | 2/1988 | Eberlein et al. | 514/215 |
| 5,317,101 | 5/1994 | Oldfield et al. | 540/495 |
| 5,324,832 | 6/1994 | Jacobsen et al. | 540/495 |

FOREIGN PATENT DOCUMENTS

| | | |
|---|---|---|
| 76072 | 4/1983 | European Pat. Off. |
| 194548 | 9/1986 | European Pat. Off. |
| 404525 | 12/1990 | European Pat. Off. |
| 443983 | 8/1991 | European Pat. Off. |
| 510526 | 10/1992 | European Pat. Off. |
| 526708 | 2/1993 | European Pat. Off. |
| 804036 | 11/1958 | United Kingdom . |
| 2228933 | 9/1990 | United Kingdom . |

OTHER PUBLICATIONS

Derwent Abstract No. 88-289069/41 Feb. 27, 1987.
Derwent Abstract No. 88-195835/28 Nov. 26, 1986.
Derwent Abstract No. 88-061295/09 Jul. 9, 1986.
Derwent Abstract No. 87-152485/22 Oct. 11, 1985.
Derwent Abstract No. 62299 E/30 Dec. 11, 1980.
Derwent Abstract No. 40927 D/23 Sep. 11, 1979.
Derwent Abstract No. 91-254550/35 Feb. 19, 1990.
Derwent Abstract 86-246709/38 Nov. 27, 1985.
Derwent Abstract No. 35012 K/15 Sep. 24, 1981.
Allen et al., "Preparation . . . antagonists", CA116(11):106284Z, p. 778, 1992.

Primary Examiner—Nicholas Rizzo
Attorney, Agent, or Firm—Timothy J. Gaul; John M. Kilcoyne

[57] ABSTRACT

Endothelin-inhibiting compounds of the formula

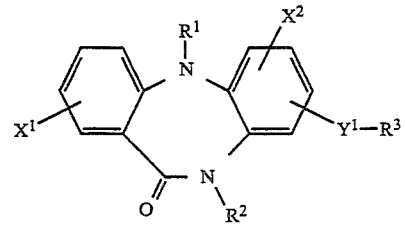

wherein:
one of $R^1$ and $R^2$ is $Y^2$-$CO_2H$ and the other is R;
R is
(a) hydrogen,
(b) alkyl,
(c) alkenyl,
(d) alkynyl,
(e) cycloalkyl,
(f) cycloalkenyl,
(g) aryl,
(h) cycloalkylalkyl,
(i) cycloalkenylalkyl, or
(j) aralkyl;
$R^3$ is aryl or heteroaryl;
$X^1$ and $X^2$ are each independently
(a) hydrogen,
(b) halo or haloalkyl,
(c) hydroxy,
(d) alkoxy,
(e) cyano,
(f) nitro, or
(g) amino, alkylamino, or dialkylamino;

and the remaining symbols are as defined in the specification.

16 Claims, No Drawings

DIBENZODIAZEPINE ENDOTHELIN ANTAGONISTS

FIELD OF THE INVENTION

This invention relates to endothelin antagonists useful, inter alia, for treatment of hypertension.

BRIEF DESCRIPTION OF THE INVENTION

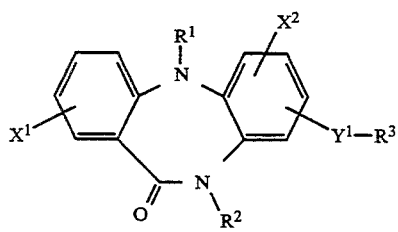

I and pharmaceutically acceptable salts, prodrugs and solvates thereof are endothelin receptor antagonists useful, inter alia, as antihypertensive agents. Throughout this specification, the above symbols are defined as follows:

one of $R^1$ and $R^2$ is $Y^2$-$CO_2H$ and the other is R;
R is
  (a) hydrogen,
  (b) alkyl,
  (c) alkenyl,
  (d) alkynyl,
  (e) cycloalkyl,
  (f) cycloalkenyl,
  (g) aryl,
  (h) cycloalkylalkyl,
  (i) cycloalkenylalkyl, or
  (j) aralkyl;
$R^3$ is aryl or heteroaryl;
$X^1$ and $X^2$ are each independently
  (a) hydrogen,
  (b) halo or haloalkyl,
  (c) hydroxy,
  (d) alkoxy
  (e) cyano,
  (f) nitro, or
  (g) amino, alkylamino, or dialkylamino;
$Y^1$ is
  (a) a single bond,
  (b) alkylene,
  (c) alkenylene,
  (d) alkynylene,
  (e) $Z^1$-O-$Z^2$,
  (f) $Z^1$-C(O)-$Z^2$,
  (g) $Z^1$-O-C(O)-$Z^2$,
  (h) $Z^1$-C(O)-O-$Z^2$,
  (i) $Z^1$-N($Z^3$)-$Z^2$,
  (j) $Z^1$-C(O)-N(H)-$Z^2$,
  (k) $Z^1$-N(H)-C-(O)-$Z^2$,
  (l) $Z^1$-C(S)-$Z^2$, or
  (m) $Z^1$-S-$Z^2$;
$Y^2$ is
  (a) alkylene,
  (b) alkenylene,
  (c) alkynylene,
  (d) $Z^1$-O-$Z^2$ (wherein $Z^2$ is other than a single bond),
  (e) $Z^1$-C(O)-$Z^2$,
  (f) $Z^1$-O-C(O)-$Z^2$
  (g) $Z^1$-C(O)-O-$Z^2$ (wherein $Z^2$ is other than a single bond),
  (h) $Z^1$-C(O)-N(H)-$Z^2$ (wherein $Z^2$ is other than a single bond),
  (i) $Z^1$-N(H)-C(O)-$Z^2$,
  (j) $Z^1$-C(S)-$Z^2$, or
  (k) $Z^1$-S-$Z^2$ (wherein $Z^2$ is other than a single bond);
$Z^1$ and $Z^2$ are each independently a single bond, alkylene, alkenylene, or alkynylene; and
$Z^3$ is hydrogen, lower alkyl, alkanoyl, aroyl, or aralkanoyl.

DETAILED DESCRIPTION OF THE INVENTION

Definition of Terms

Listed below are definitions of terms used in this specification. These definitions apply to the terms as used throughout this specification, individually or as part of another group, unless otherwise limited in specific instances.

The terms "alkyl" and "alkoxy" refer to straight or branched chain hydrocarbon groups having 1 to 10 carbon atoms. The terms "lower alkyl" and "lower alkoxy" refer to groups of 1 to 4 carbon atoms, which are preferred, The term "aryl" or "ar-" refers to phenyl, naphthyl, and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g.,-$(CH_2)_x$- wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are -CH=CH-CH=CH-, -$CH_2$-CH=CH-, -$CH_2$-CH=CH-$CH_2$-, -C($CH_3$)$_2$CH=CH-, and -CH($C_2H_5$)-CH=CH.

The term "alkynylene" refers to a straight chain bridge of 2 to 5 carbon atoms having one or two triple bonds that is connected by single bonds and may be substituted with 1 to 3 lower alkyl groups. Exemplary alkynylene groups are -C≡C-, -$CH_2$-C≡C-, -CH($CH_3$)-C≡C-, and -C≡C-CH($C_2H_5$)$CH_2$-.

The suffix "-oyl" refers to -C(O)-. Thus, the terms "alkanoyl", "aroyl" and "aralkanoyl" refer to groups of the formula -C(O)alkyl, -C(O)aryl, and -C(O)-alkaryl, respectively.

The terms "cycloalkyl" and "cycloalkenyl" refers to cyclic hydrocarbon groups of 3 to 8 carbon atoms.

The terms "halogen" and "halo" refers to fluorine, chlorine, bromine and iodine. The term "haloalkyl" refers to alkyl groups substituted with one to five halo atoms, such as trifluoromethyl and pentafluoroethyl.

The term "heteroaryl" refers to monocyclic and bicyclic aromatic rings of 4 to 10 atoms, having 1 to 4 heteroatoms in the ring selected from 1 to 4 nitrogen and/or 1 or 2 oxygen or sulfur atoms. Exemplary heteroaryl groups are pyrrolyl, pyrazolyl, imidazolyl, pyridyl, pyrimidyl, puryl, quinolyl, isoquinolyl, indolyl, triazolyl, benzotriazolyl, quinoxalyl, quinozolyl, oxazolyl, thiazolyl, furyl, thiophenyl, and the like.

The compounds of formula I form salts which are also within the scope of this invention. Pharmaceutically acceptable (i.e., non-toxic, physiologically acceptable) salts are preferred, although other salts are also useful, e.g, in isolating or purifying the compounds of this invention.

The compounds of formula I may form salts with alkali metals such as sodium, potassium and lithium, with alkaline earth metals such as calcium and magnesium, with organic bases such as dicyclohexylamine, benzathine, N-methyl-D-glucamide and hydrabamine, and with amino acids such as arginine, lysine and the like. Such salts may be obtained by reacting compound I with the desired ion in a medium in which the salt precipitates or in an aqueous medium followed by lyophilization.

When its substituents comprise a basic moiety, such as amino or substituted amino, compound I may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate, and various other sulfonates, nitrates, phosphates, borates, acetates, tartrates, maleates, citrates, succinates, benzoates, ascorbates, salicylates, and the like. Such salts may be formed by reacting compound I in an equivalent amount of the acid in a medium in which the salt precipitates or in an aqueous medium followed by lyophilization.

In addition, when compound I's substituents comprise a basic moiety such as amino, zwitterions ("inner salts") may be formed.

Compound I may also have prodrug forms, such as ester, acetal and/or mixed acetal derivatives of compound I. For example, such derivatives have been documented in Design of Prodrugs, edited by H. Bundgard, (Elsevier, 1985) and Methods in Enzymology, Vol. 42, p. 309–396, edited by K. Widder et al. (Academic Press, 1985). Any moiety that will be cleaved in vivo to provide an acidic moiety is a prodrug within the scope and spirit of the invention.

It should further be understood that solvates (e.g., hydrates) of compound I are also within the scope of the present invention. Methods of solvation are generally known in the art.

Certain of the substituents of compound I may contain asymmetric carbon atoms. Such compounds of formula I may exist, therefore, in enantiomeric and diasteromeric forms and in racemic mixtures thereof. All are within the scope of this invention.

Preferred Moieties

For compound I, it is preferred that:
one of $R^1$ and $R^2$ is alkyl;
$R^3$ is aryl or indolyl;
$Y^1$ is alkylene, $Z^1$-O-$Z^2$, $Z^1$-N($Z^3$)-$Z^2$, or $Z^1$-N(H)-C(O)-$Z^2$;
$Y^2$ is alkylene, alkenylene, or alkynylene; and
$Z^1$ and $Z^2$ are each independently a single bond or alkylene.

It is most preferred that:
$R^1$ is alkyl;
$R^2$ is $Y^2$-$CO_2H$; and
$Y^2$ is alkylene.

Use and Utility

The compounds of formula I are antagonists of ET-1, ET-2, and/or ET-3 and are useful in treatment of all endothelin-dependent disorders. They are thus useful as antihypertensive agents. By the administration of a composition having one (or a combination) of the compounds of this invention, the blood pressure of a hypertensive mammalian (e.g., human) host is reduced.

The compounds of the present invention are also useful in the treatment of disorders related to renal, glomerular, and mesangial cell function, including chronic renal failure, glomerular injury, renal damage secondary to old age, nephrosclerosis (especially hypertensive nephrosclerosis), nephrotoxicity (including nephrotoxicity related to imaging and contrast agents), and the like. The compounds of this invention may also be useful in the treatment of disorders related to paracrine and endocrine function.

The compounds of the present invention are also useful in the treatment of endotoxemia or endotoxin shock.

The compounds of the present invention are also useful as anti-ischemic agents for the treatment of, for example, heart, renal and cerebral ischemia and the like.

In addition, the compounds of this invention may also be useful as anti-arrhythmic agents; anti-anginal agents; anti-fibrillatory agents; anti-asthmatic agents; therapy for myocardial infarction; therapy for peripheral vascular disease (e.g., Raynaud's disease); anti-atherosclerotic agents; treatment of cardiac hypertrophy (e.g., hypertrophic cardiomyopathy); treatment of pulmonary hypertension; additives to cardioplegic solutions for cardiopulmonary bypasses; adjuncts to thrombolytic therapy; treatment of central nervous system vascular disorders, such as stroke, migraine, and subarachnoid hemorrhage; treatment of central nervous system behavioral disorders; treatment of gastrointestinal diseases, such as ulcerative colitis and Crohn's disease; anti-diarrheal agents; regulation of cell growth; and treatment of hepatoxicity and sudden death.

The compounds of this invention can also be formulated in combination with endothelin converting enzyme (ECE) inhibitors, such as phosphoramidon; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril, and salts of such compounds; neutral endopeptidase (NEP) inhibitors; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; thrombolytic agents such as tissue plasminogen activator (tPA), recombinant tPA, streptokinase, urokinase, prourokinase, and anisoylated plasminogen streptokinase activator complex (APSAC). If formulated as a fixed dose, such combination products employ the compounds of this invention within the dosage range described below and the other pharmaceutically active agent within its approved dosage range. The compounds of this invention may also be formulated with or useful in conjunction with antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carder, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions of suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

Process of Preparation

The compounds of the present invention may be prepared as follows.

When $Y^1$ is $Z^1$-S-$Z^2$, $Z^1$-C(O)-$Z^2$, $Z^1$-O-C(O)-$Z^2$, $Z^1$-C(O)-O-$Z^2$, $Z^1$-C(S)-$Z^2$, $Z^1$-C(O)N(H)-$Z^2$, or $Z^1$-O-$Z^2$ (as in Examples 1 and 2 hereinafter), an amino-nitro-phenyl

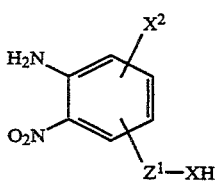

II (wherein X is -O-,-S-,-C(O)-,-O-C(O)-,-C(O)-O-,-C(O)N(H)- or -C(S)-) undergoes a halogen exchange by treatment with sodium nitrite in an aqueous acid (e.g., sulfuric acid) at about 0° to 10° C., followed by a halo salt (e.g., potassium bromide) in the presence of copper powder at about 75° to 85° C. to form a halo-nitro-phenyl

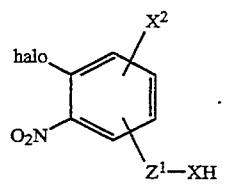

III

Halo-nitro-phenyl III reacts with a compound IV

L-$Z^2$-$R^3$ (wherein L is a leaving group such as halo) in an organic solvent (e.g., dimethylformamide) in the presence of a base (e.g., potassium carbonate) at about 20° to 30° C. to form

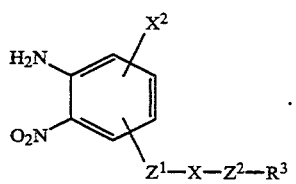

V

Compound V reacts with anthranilic acid or a derivative thereof substituted with $X^1$ in an organic solvent (e.g., n-amyl alcohol) in the presence of a base (e.g., potassium carbonate) and copper powder to form a diphenylamine

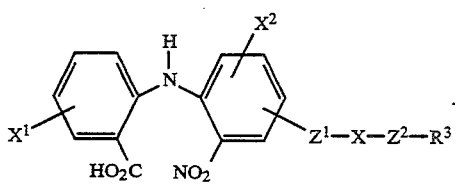

VI

Diphenylamine VI is treated with a reducing agent (e.g., sodium hydrosulfite) in the presence of a base (e.g., ammonium hydroxide) to form a diamine

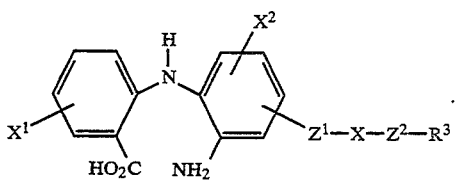

VII

Diamine VII undergoes cyclodehydration in an organic solvent (e.g., xylene) in an inert atmosphere (e.g., argon) to form a dibenzodiazepine

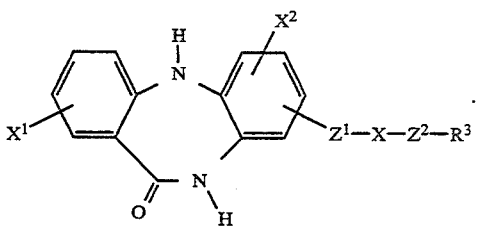

VIII

Dibenzodiazepine VIII is treated with a base (e.g., sodium hydride suspended in mineral oil) in an organic solvent (e.g., dimethylformamide) at about 55° to 65° C., followed by a coupling agent

IX

L-Y²-CO₂R⁴

(wherein R⁴ is an ester-forming group, such as alkyl, aryl, or aralkyl) at about 75° to 85° C. to form a dibenzodiazepine ester

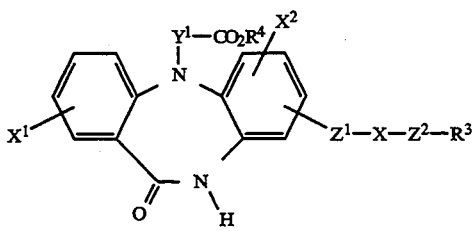

Xa and/or

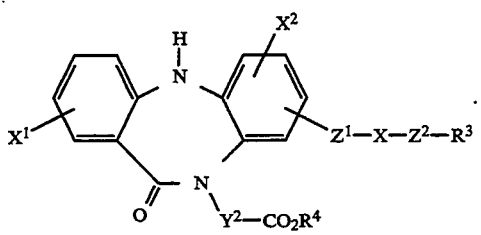

Xb

Esters Xa and/or Xb are de-esterified by treatment with a base (e.g., aqueous sodium hydroxide) in an organic solvent (e.g., methanol) to form compound I wherein one of R¹ and R² is hydrogen. Esters Xa or Xb or the associated acids may be treated with a base (e.g., sodium hydride suspended in mineral oil), followed by

XI

L-R (wherein R is other than hydrogen) at about 55° to 65° C. to form compound I wherein R is other than hydrogen.

When Y¹ is alkylene, alkenylene, or alkynylene (as in Examples 4 and 5 hereinafter), a halo-nitro-phenyl

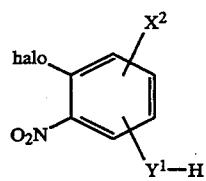

XII is treated as described for compounds V through X to form

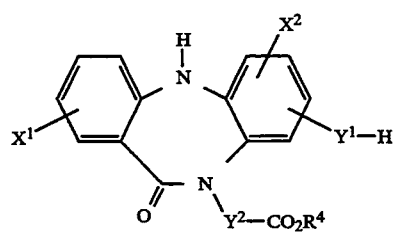

XIII wherein Y¹ is alkylene, alkenylene, or alkynylene.

Compound XIII is treated with an acylating agent (e.g., trifluoroacetic anhydride) in an organic solvent (e.g., methylene chloride) under an inert atmosphere (e.g., argon) at about 0° C., followed by warming to about 20° to 30° C., to form

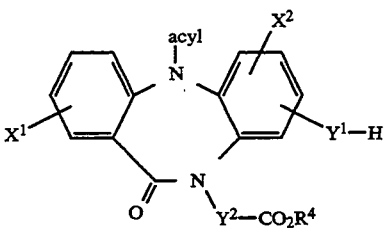

XIV wherein the acyl group is, for example, alkanoyl or haloalkanoyl.

Compound XIV is treated with a halogenating agent (e.g., N-bromosuccinimide) in an organic solvent (e.g., carbon tetrachloride) in the presence of light and a radical initiator (e.g., benzoyl peroxide) in an inert atmosphere to form a halogenated compound

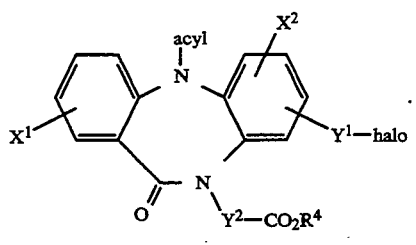

XV

Halo compound XV is alkylated in an organic solvent (e.g., dioxane) in the presence of a catalyst (e.g., silver-(I)oxide) to form compound Xb wherein Y¹ is alkylene, alkenylene, or alkynylene. This compound is treated as described for compounds Xa and Xb above to form the associated compound I wherein Y¹ is alkylene, alkenylene, or alkynylene.

When Y¹ is Z¹-N(H)-C(O)-Z² (as in Examples 6, 7 and 8 hereinafter), an amino-nitro-phenyl

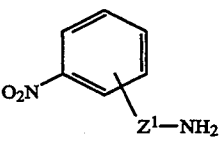

XVI is treated with a halogenating agent (e.g., 2,4,6-tetrabromo-2,5-cyclohexadien-1-one) at about −15° to −5° C., followed by warming to 20° to 30° C., in an organic solvent (e.g., chloroform) to form a halo-nitro-aminophenyl

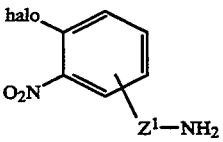

XVII

Compound XVII is cycloprotected by treatment with, for example phthalic anhydride in an organic solvent (e.g., xylene) to form

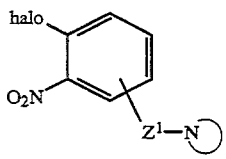

wherein

is a heteroaryl group attached to the phenyl ring through a ring nitrogen. Compound XVIII is treated as described for compounds V to X to form

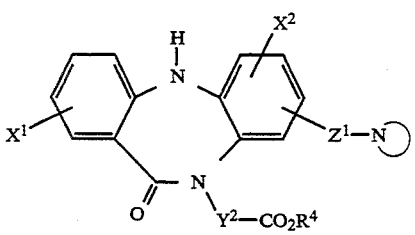

XIX

Compound XIX may be de-esterified as described for compounds Xa and Xb to form compound I wherein $R^3$ is

Alternatively, compound XIX undergoes (1) reductive amination or alkylation as described for the reaction of compounds X and XI and (2) amino-deprotection by, for example, hydrazine monohydrate in an organic solvent such as methanol, to form

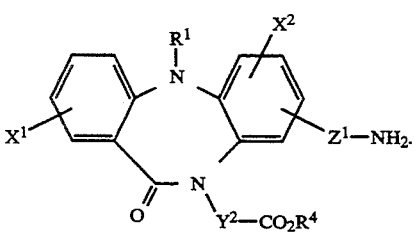

XX

Compound XX then undergoes an amide bond-forming reaction to form

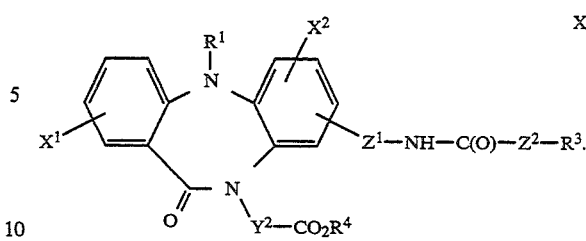

XXI

The amide bond may be formed, for example, by treatment with an acid chloride such as 1H-indole-3-acetyl chloride in an organic solvent such as methylene chloride. The resulting compound XXI may be de-esterified as described for compounds Xa and Xb to form compound I.

When $Y^1$ is $Z^1$-N($Z^3$)-$Z^2$ (as in Example 9 hereinafter), compound XX is treated with an aldehyde XXII

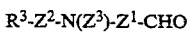

$R^3$-$Z^2$-N($Z^3$)-$Z^1$-CHO in the presence of a buffer such as sodium acetate at about 40° to 50° C. to form compound XXI wherein $Y^1$ is $Z^1$-N($Z^3$)-$Z^2$. This compound is de-esterified as described for compounds Xa and Xb to form compound I.

The invention will now be further described by the following working examples, which are preferred embodiments of the invention. These examples are meant to be illustrative rather than limiting.

EXAMPLE 1

5,11-Dihydro-8-(1-naphthalenylmethoxy)-11-oxo-10H-dibenzo[b,e][1,4]diazepine-10-acetic acid

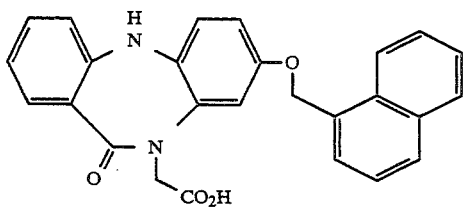

A. 2-Bromo-5-(1-naphthalenylmethoxy)-nitrobenzene

To a solution of 4.0 g (18.3 mmol) of 4-bromo-3-nitrophenol in 25 mL of dimethylformamide, 4.87 g (22.0 mmol) of 1-bromomethyl naphthalene and 3.04 g (22.0 mmol) of potassium carbonate were added and the mixture was stirred at room temperature overnight. The mixture was poured into 250 mL of ice/water and the precipitate was filtered and dried to afford compound A as a tan solid (6.1 g, 92%).

Melting point: 124°–126° C.

B. 2-Nitro-4-(1-naphthalenylmethoxy)diphenylamine-2'-carboxylic acid

To a solution of 6.9 g (19.3 mmol) of compound A and 2.64 g (19.3 mmol) of anthranilic acid in 50 mL of n-amyl alcohol, 2.66 g (19.3 mmol) of solid potassium carbonate and 400 mg of copper powder were added and the mixture was refluxed under argon for 6 hours. The solution was evaporated in vacuo and the residue was dissolved in 200 mL of water and filtered. The filtrate was acidified to pH 4 using glacial acetic acid and the precipitate was filtered and dried to afford compound B as a red solid (7.6 g, 95%).

Melting point: 210°–220° C. (d)

C. 2-Amino-4-(1-naphthalenylmethoxy)-diphenylamine-2'-carboxylic Acid

To a solution of 7.0 g (16.9 mmol) of compound B in 200 mL of 2 N aqueous ammonum hydroxide, 8.8 g (50.6 mmol) of sodium hydrosulfite was added in portions over 30 minutes. The solution was stirred at room temperature for 3 hours. The mixture was filtered and the filtrate was acidified with glacial acetic acid and the precipitate was filtered and dried to afford compound C as a light grey solid (5.7 g, 88%).

Melting point: 208°–211° C. (d).

D. 5,11-Dihydro-8-(1-napthalenylmethoxy)-11-oxo-10H-dibenzo[b,e]-1,4-diazepine

A suspension of 5.0 g (13.0 mmol) of compound C in 200 mL of xylenes was refluxed under argon for 48 hours under continuous removal of water. The solution was concentrated to about 30 mL and cooled to room temperature and filtered to provide 2.3 g (48%) of compound C as a light brown solid.

Melting point: greater than 220° C.

E. 5,11-Dihydro-8-(1-napthalenylmethoxy)-11-oxo-10H-dibenzo[b,e]-1,4-diazepine-10-acetic acid methyl ester To a solution of 0.5 g (1.36 mmol) of compound D in 10 mL of dry dimethylformamide at room temperature under argon, sodium hydride (57 mg, 1.43 mmol, 60% suspension in mineral oil) was added and the mixture was stirred at 60° C. for 30 minutes. The solution was cooled to room temperature and 0.25 g (1.64 mmol) of methyl bromoacetate was added and the mixture was stirred at 80° C. for 24 hours. The solution was cooled to room temperature and poured into 300 mL of ice/water and filtered to provide 1.91 g of a light grey solid. This material was chromatographed on 100 g of silica gel using 2:1 hexanes/ethyl acetate to afford 0.41 g (69%) of compound E as a light brown foam.

Melting point: 85°–92° C. (amorphous).

F. 5,11-Dihydro-8-(1-napthalenylmethoxy)-11-oxo-10H-dibenzo[b,e]-1,4-diazepine-10-acetic acid:

To a solution of 0.35 g (0.67 mmol) of compound E in 10 mL of methanol at room temperature, 5 mL of 1 N aqueous sodium hydroxide was added and the mixture was stirred at 60° C. for 2 hours. The solution was concentrated and diluted with 25 mL of water and filtered. The filtrate was acidified to pH 2 using 1 N aqueous hydrochloric acid and the precipitate was filtered and dried to afford Example 1 as a white solid (0.26 g, 77%).

Melting point: 209°–210° C.

Analysis for $C_{26}H_{20}N_2O_4 \cdot 0.26\ H_2O$ Calc'd: C 72.76; H 4.82; N 6.53 Found: C 72.76; H 4.55; N 6.53

EXAMPLE 2

5,11-Dihydro-8-(phenylmethoxy)-11-oxo-10H-dibenzo[b,e][1,4]diazepine-10-acetic acid

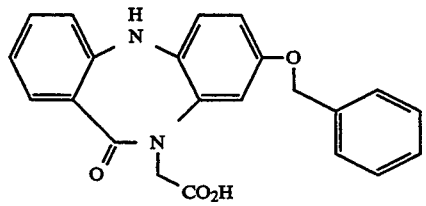

A. 2-Bromo-5-benzyloxy-nitrobenzene

To a solution of 6.2 g (28.4 mmol) of 4-bromo-3-nitrophenol in 30 mL of dimethylformamide, 5.35 g (31.3 mmol) of benzyl bromide and 4.32 g (31.3 mmol) of potassium carbonate were added and the mixture was stirred at room temperature overnight. The mixture was poured into 300 mL of ice/water and extracted with ethyl acetate (3×150 mL) and the combined organic solutions were dried and evaporated to provide 8.7 g (100%) of compound A as a straw-colored oil.

B. 2-Nitro-4-benzyloxy-diphenylamine-2'-carboxylic acid

Compund B was prepared as a red solid as described for compound B of Example 1, using compound A of Example 2 in place of compound A of Example 1.

Melting point: 185°–190° C.

C. 2-Amino-4-benzyloxy-diphenylamine-2'-carboxylic acid

Compound C was prepared from the above compound B as a light grey solid as described for compound C of Example 1.

D. 5,11-Dihydro-8-(1-phenylmethoxy)-10H-11-oxo-dibenzo[b,e]-1,4-diazepine

A suspension of 4.5 g (13.45 mmol) of compound C in 200 mL of xylenes was refluxed under argon for 16 hours under continuous removal of water. The solution was evaporated and the residue was chromatographed on 200 g of silica gel using 2:1 hexanes/ethyl acetate to provide 2.16 g (51%) of compound D as a light brown solid.

Melting point: 153°–155° C.

E. 5,11-Dihydro-8-(1-phenylmethoxy)-10H-11-oxo-dibenzo[b,e]-1,4-diazepine-10-acetic acid methyl ester Compound E, a light brown foam, was prepared from the above compound D as described for compound E of Example 1. The reaction temperature was kept at 60° C. for 24 hours. The chromatography solvent was 2% methanol/methylene chloride.

Melting point: 70°–77° C. (amorphous).

F. 5,11-Dihydro-8-(1-phenylmethoxy)-10H-11-oxo-dibenzo[b,e]-1,4-diazepine-10-acetic acid To a solution of 0.26 g (0.67 mmol) of compound E in 10 mL of methanol at room temperature, 5 mL of 1 N aqueous sodium hydroxide was added and the mixture was stirred at 60° C. for 2 hours. The solution was concentrated and diluted with 25 mL of water and washed once with 25 mL of ethyl acetate. The aqueous layer was acidified to pH 2 using 1 N aqueous hydrochloric acid and the precipitate was filtered and dried to afford Example 2 as a white solid (0.18 g, 72%).

Melting point: 115°–118° C.

Analysis for $C_{22}H_{18}N_2O_4 \cdot 0.24\ H_2O$ Calc'd: C 69.61; H 4.93; N 7.38 Found: C 69.61; H 4.78; N 7.38

EXAMPLE 3

5,11-Dihydro-8-(1-naphthalenylmethoxy)-11-oxo-5-propyl-10H-dibenzo[b,e][1,4]diazepine-10-acetic acid

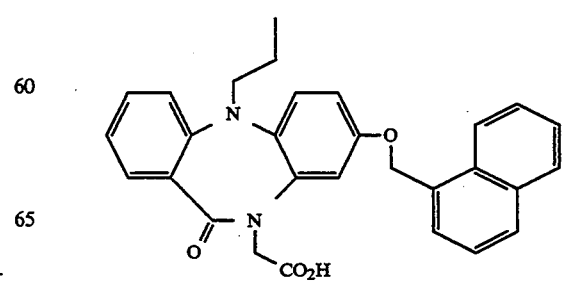

To a solution of 0.22 g (0.52 mmol) of Example 1 in 3 mL of dimethylformamide under argon at room temperature, sodium hydride (0.046 g, 1.14 mmol, 60% suspension in mineral oil) was added and the solution was stirred for 20 minutes. Then, 1-iodopropane (0.11 g, 0.62 mmol) was added and the mixture was stirred at 60° C. for 48 hours. The mixture was cooled to room temperature and diluted with 20 mL of water. The solution was acidified to pH 2 using dilute aqueous hydrochloric acid. The white solid was filtered and dried (0.19 g). This material was chromatographed on 50 g of silica gel using 5% methanol in dichloromethane to provide 0.1 g (42%) of Example 3 as a light brown solid.

Melting point: 120°–125° C.

Analysis for $C_{29}H_{26}N_2O_4$ Calc'd: C 74.66; H 5.62; N 6.00 Found: C 74.50; H 5.88; N 5.81

EXAMPLE 4

5,11-Dihydro-8-[(1H-indol-3-yl)methyl]-11-oxo-5-propyl-10H-dibenzo[b,e][1,4]-diazepine-10-acetic acid

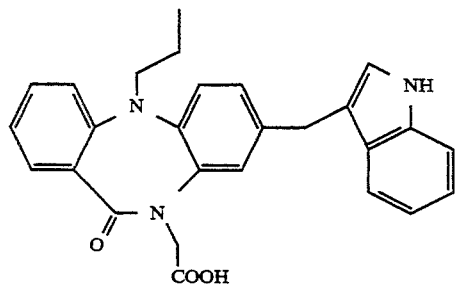

A.  5,11-Dihydro-8-(1H-indol-3-ylmethyl)-11-oxo-10H-dibenzo-[b,e][1,4]-diazepine-10-acetic acid, methyl ester To a solution of 0.5 g (0.99 mmol) of compound E from Example 5 in 12 mL of methanol under argon at room temperature, 4 mL of 10% aqueous potassium carbonate was added and the mixture was stirred for 30 minutes. The solution was concentrated to about 5 mL and diluted with 50 mL of water and extracted with 3×50 mL of ethyl acetate. The combined organic extracts were washed once with 100 mL of brine and dried and evaporated to provide 0.41 g (100%) of compound 2 as a white foam. $R_f$=0.19 (hexanes/ethyl acetate 1:1).

B.  5,11-Dihydro-8-(1H-indol-3-ylmethyl)-11-oxo-5-propyl-10H-dibenzo[b,e][1,4]-diazepine-10-acetic acid, methyl ester To a solution of 0.35 g (0.85 mmol) of compound A in 25 mL of 1,2-dichloroethane, propionaldehyde (0.198 g, 3.4 mmol) and glacial acetic acid (0.31 g, 5.1 mmol) were added and the solution was stirred at room temperature under argon for 5 minutes. Sodium triacetoxyborohydride (0.72 g, 3.4 mmol) was added to the mixture in one portion and the solution was stirred at room temperature for 72 hours. The mixture was diluted with 25 mL of methylene chloride and washed with 25 mL of 5% aqueous sodium hydrogen carbonate and dried and evaporated. The residue was chromatographed on silica gel using 3:1 hexanes/ethyl acetate to afford 0.28 (73%) of compound B as a light brown foam. $R_f$=0.30 (hexanes/ethyl acetate, 1:1).

C.  5,11-Dihydro-8-[(1H-indol-3-yl)methyl]-11-oxo-5-propyl-10H-dibenzo[b,e][1,4]-diazepine-10-acetic acid To a solution of 0.24 g (0.54 mmol) of compound B in 15 mL of methanol, 5 mL of 1 N aqueous sodium hydroxide was added and the mixture was stirred at room temperature for 4 hours and at 40° C. for an additional 1 hour. The solution was concentrated to about 5 mL and diluted with 15 mL of water. The solution was acidified to pH 1 using 1 N aqueous hydrochloric acid and the white solid thus obtained was filtered and dried (0.2 g). This material was chromatographed on 20 g of silica gel using 2% methanol/methylene chloride to provide 0.11 g of Example 4 as a light orange foam.

Melting point: foams at 115°–120° C., melts at 155°–165° C. (amorphous).

Analysis for $C_{27}H_{25}N_3O_3 \cdot 1.18\ H_2O$ Calc'd: C 70.38; H 5.98; N 9.12 Found: C 70.51; H 5.61; N 8.99

EXAMPLE 5

5,11-Dihydro-8-[(1H-indol-3-yl)methyl]-11-oxo-10H-dibenzo[b,e][1,4]diazepine-10-acetic acid

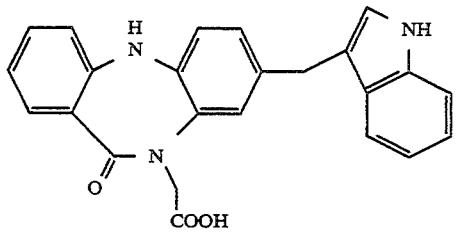

A.  5,10-Dihydro-8-methyl-11H-dibenzo[b,e][1,4]diazepine-11-one

Compound A was prepared as described for compounds B, C and D of Example 1 using 1-bromo-4-methyl-2-nitrobenzene in place of compound A of Example 1.

Melting point: 196°–197° C.

B.  5,11-Dihydro-8-Methyl-11-oxo-10H-dibenzo[b,e][1,4]-diazepine-10-acetic acid methyl ester Compound B was prepared as a light yellow foam as described for compound E of Example 1, using compound A above in place of compound D from Example 1.

Melting point: 180°–186° C. (amorphous).

C. 5,11-Dihydro-8-methyl-11-oxo-5-(trifluoroacetyl)-10H-dibenzo[b,e][1,4]diazepine-10-acetic acid, methyl ester To a solution of compound B (3.90 g, 13.2 mmol) and triethylamine (1.60 g, 15.8 mmol) in 150 mL of methylene chloride at 0° C. under argon, trifluoroacetic anhydride (3.32 g, 15.8 mmol) was added over 15 minutes, and the solution was stirred at 0° C. for 30 minutes. The mixture was warmed to room temperature and stirred for an additional 2 hours. The solution was washed with 200 mL of water and dried and evaporated to provide 5.2 g of compound C as a foam. $R_f$=0.36 (hexanes/ethyl acetate, 1:1).

D.  8-(Bromomethyl)-5,11-dihydro-11-oxo-5-(trifluoroacetyl)-10H-dibenzo[b,e][1,4]-diazepine-10-acetic acid, methyl ester To a solution of compound C in 200 mL of carbon tetrachloride, N-bromosuccinimide (2.31 g, 13.0 mmol) and benzoyl peroxide (0.3 g) were added and the solution was refluxed for 6 hours under argon while being irradiated with an ultraviolet sunlamp. The mixture was filtered, the filtrate was concentrated, and the residue (6.5 g) was chromatographed on 200 g of silica gel using 3:1 hexanes/ethyl acetate to provide 3.9 g (64%) of compound D as a white foam. R$_f$=0.38 (hexanes/ethyl acetate, 1:1).

E. 5,11-Dihydro-8-(1H-indol-3-ylmethyl)-11-oxo-5-(trifluoroacetyl)-10H-dibenzo[b,e][1,4]-diazepine-10-acetic acid, methyl ester To a solution of 3.1 g (6.58 mmol) of compound D in 100 mL of dioxane, indole (0.93 g, 7.89 mmol) and silver(I) oxide (1.83 g, 7.89 mmol) were added and the mixture was stirred at 80° C. under argon for 24 hours. The mixture was filtered through a pad of Celite, the filtrate was concentrated and the residue was chromatographed on 200 mL of silica gel using 2:1 hexanes/ethyl acetate to provide 1.26 g (38%) of compound E as a pink foam. R$_f$=0.26 (hexanes/ethyl acetate, 1:1).

F. 5,11-Dihydro-8-[(1H-indol-3-yl)methyl]-11-oxo-10H-dibenzo[b,e][1,4]diazepine-10-acetic acid To a solution of 0.4 g (0.79 mmol) of compound E in 20 mL of methanol, 1 N aqueous sodium hydroxide (7 mL) was added and the mixture was stirred at room temperature under argon for 24 hours. The mixture was concentrated to about 5 mL, diluted with 20 mL of water and the solution was acidified to pH 1 using 1 N aqueous hydrochloric acid. The white solid was filtered and dried (0.32 g) and a portion of this sample (0.17 g) was purified on silica gel (20 g) using 3% methanol/methylene chloride to provide 0.11 g of Example 5 as a pink foam.

Melting point: 160°-170° C. (with foaming at. 105°-110° C.).

Analysis for C$_{24}$H$_{19}$N$_3$O$_3$·1.43 H$_2$O Calc'd: C 68.13; H 5.21; N 9.95 Found: C 68.65; H 5.15; N 9.41

EXAMPLE 6

5,11-Dihydro-8-[[(1H-indol-3-yl)acetyl]amino]-11-oxo-5-propyl-10H-dibenzo[b,e][1,4]diazepine-10-acetic acid, monosodium salt

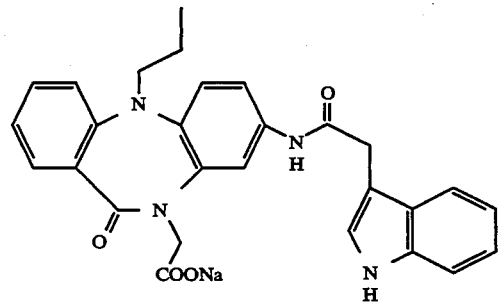

A. 4-Bromo-3-nitrobenzenamine

A solution of 3-nitroaniline (7.60 g, 55 mmol) in 400 mL chloroform was cooled to −10° C., and 2,4,4,6-Tetrabromo-2,5-cyclohexadien-1-one (24.79 g, 60.5 mmol) was added in approximately 0.5 g portions. The cooling bath was removed, and the reaction mixture was allowed to warm to room temperature over a 30-minute period and was then stirred at room temperature overnight. The reaction mixture was washed with 2 N sodium hydroxide, water and dried (magnesium sulfate) and concentrated. The residue was recrystallized from ethyl acetate/hexanes to afford 7.7 g of compound A as a yellow solid. The mother liquid was concentrated and the residue was chromatographed on silica gel eluting with hexanes:ethyl acetate (5:1 to 3:1) to give an additional 1.4 g (75%) of compound A.

B. 2-(4-Bromo-3-nitrophenyl)-1,3-dihydro-1H-isoindole-1,3(2H)-dione

A mixture of compound A (8.53 g, 39.3 mmol), phthalic anhydride (8.73 g, 59.0 mmol) and 400 mL of xylene was refluxed for 24 hours. About two thirds of the solvent was removed by distillation, the residue was cooled to room temperature, and 200 mL of hexane was added. The precipitate was collected by filtration. The solid was dissolved in ethyl acetate and washed with saturated sodium hydrogen carbonate and water. The organic layer was dried (magnesium sulfate) and concentrated to afford compound B (12 g, 88%). R$_f$=0.72 (silica gel; hexanes:ethyl acetate, 1:1).

C. 2-[[4-(1,3-Dihydro-1,3-dioxo-2H-isoindol-2-yl)-2-nitrophenyl]amino]benzoic acid To a mixture of compound B (12.03 g, 34.6 mmol) and anthranilic acid (4.75 g, 34.6 mmol) in 138 mL of n-amyl alcohol, solid potassium carbonate (4.79 g, 34.6 mmol) and copper powder (726 mg, 11.4 mmol) were added and the mixture was refluxed under argon for 7 hours. The solvent was evaporated to give crude compound C as a red solid.

D. 2-[[2-Amino-4-(1,3-dihydro-1,3-dioxo-2H-isoindol-2-yl)-phenyl]amino]benzoic acid To a mixture of compound C in 450 mL of 7.5% aqueous ammonium hydroxide, sodium hydrosulfite (21.29 g, 104 mmol) was added in portions over 30 minutes. The reaction was stirred at room temperature for 3.5 hours. The mixture was acidified with 6 N hydrochloric acid to about pH 4 and filtered to afford compound D as a solid.

E. 5,10-Dihydro-8-[[(1,3-dihydro-1,3-dioxo-2H-isoindol-2-yl)-11H-dibenzo[b,e][1,4]diazepine-11-one A suspension of compound D in 800 mL of xylene was refluxed under argon for 4 days under continuous removal of water. The reaction mixture was chromatographed on silica gel eluting with methylene chloride:ethyl acetate (8:1 to 5:1) to provide compound E as a yellow solid (3.64 g, 30% yield for three steps). R$_f$=0.66 (silica gel; hexane:ethyl acetate, 1:2).

F. 5,11-Dihydro-8-[[(1,3-dihydro-1,3-dioxo-2H-isoindol-2-yl)-11-oxo-10H-dibenzo[b,e][1,4]-diazepine-10-acetic acid, methyl ester To a solution of compound E (3.55 g, 10 mmol) in 67 mL dry dimethylformamide at 0° C. under argon, sodium hydride (520 mg, 13 mmol, 60% suspension in mineral oil) was added. The mixture was stirred at 60° C. for 30 minutes. The solution was cooled to room temperature and methyl bromoacetate (1.99 g, 13 mmol) was added and the mixture was heated at 80° C. for 20 hours. The solution was cooled to room temperature, poured into 1600 mL of iced aqueous ammonium chloride and the solution was extracted with methylene chloride. The organic extracts were concentrated and the residue was chromatographed on silica gel using 20:1 methylene chloride/ethyl acetate to afford compound F as a yellow solid (2.75 g, 65%).

Melting point: 116°-123° C.

G. 5,11-Dihydro-8-[[(1,3-dihydro-1,3-dioxo-2H-isoindol-2-yl)-11-oxo-5-propyl-10H-dibenzo-[b,e][1,4]diazepine-10-acetic acid, methyl ester A mixture of compound F (2.73 g, 6.38 mmol), propionaldehyde (1.48 g, 25.5 mmol), sodium triacetoxyborohydride (5.40 g, 25.5 mmol) and acetic acid (3.06 g, 51.0 mmol) in 100 mL of 1,2-dichloroethane was stirred at room temperature for 64 hours. The reaction mixture was poured into water, neutralized with sodium hydrogen carbonate and extracted several times with methylene chloride. The organic extracts were concentrated and the residue was chromatographed on silica gel eluting with 50:1 to 10:1 methylene chloride/ethyl acetate to afford unconsumed staring compound F (0.80 g, 1.87 mmol) and compound G as a white solid (1.85 g, 67%).

Melting point: 97°–102 ° C.

H. 8-Amino-5,11-dihydro-11-oxo-5-propyl-10H-dibenzo[b,e][1,4]-diazepine-10-acetic acid, methyl ester To a solution of compound G (1.0 g, 2.13 mmol) in 14 mL of methanol, hydrazine monohydrate (133 mg, 2.66 mmol) was added. The reaction was stirred at room temperature for 2.5 hours. The solid was removed by filtration. The filtrate was concentrated and the residue was chromatographed on silica gel eluting with 50:50:0.2 hexane/ethyl acetate/triethylamine to provide compound H as a yellow solid (0.65 g, 90%).

Melting point: 176°–178° C.

I. 5,11-Dihydro-8-[(1H-indol-3-ylacetyl)amino]-11-oxo-5-propyl-10H-dibenzo[b,e][1,4]diazepine-10-acetic acid,methyl ester To indole-3-acetic acid (186 mg, 1.06 mmol) in 3.5 mL of methylene chloride and 0.009 mL of dimethylformamide, oxalyl chloride (2 M in methylene chloride, 0.64 mL, 1.27 mmol) was added. The mixture was stirred at room temperature for 1 hour and concentrated to give 1H-indole-3-acetyl chloride.

To a solution of 1H-indole-3-acetyl chloride and compound H (180 mg, 0.53 mmol) in 1.8 mL of methylene chloride, triethylamine (188 mg, 1.86 mmol) was added. The mixture was stirred for 80 minutes, poured into aqueous ammonium chloride and extracted with methylene chloride. The organic extracts were concentrated and the residue was chromatographed on silica gel using 60:10:0.14 methylene chloride/ethyl acetate/triethylamine to provide compound I (155 mg, 59%).

J. 5,11-Dihydro-8-[[(1H-indol-3-yl)acetyl]amino]-11-oxo-5-propyl-10H-dibenzo[b,e][1,4]-diazepine-10-acetic acid, monosodium salt Compound I (155 mg, 0.31 mmol) was dissolved in 6 mL of methanol and 3 mL of tetrahydrofuran. Sodium hydroxide (1 N, 1.6 mL) was added, the mixture was heated at 50° C. for 1 hour, concentrated under vacuum and the residue was chromatographed on HP-20 eluted with a gradient from water to 80% aqueous acetone to provide Example 6 as a white solid (117 mg, 75%).

Melting point: greater than 200° C. (dec.).

Analysis for $C_{28}H_{25}N_4O_4Na \cdot 2.3\ H_2O$ Calc'd: C 61.60; H 5.47; N 10.26 Found: C 61.89; H 5.30; N 9.93

EXAMPLE 7

5,11-Dihydro-8-[[(1H-indol-3-yl)carbonyl]amino]-11-oxo-5-propyl-10H-dibenzo[b,e][1,4]diazepine-10-acetic acid, monosodium salt

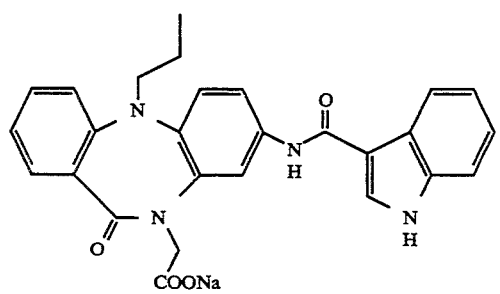

A. 5,11-Dihydro-8-[(1H-indol-3-ylcarbonyl)amino]-11-oxo-5-propyl-10H-dibenzo[b,e][1,4]-diazepine-10-acetic acid,methyl ester Compound A was prepared as described in part I of Example 6, using 1H-indole-3-acetyl chloride. Chromatography was on silica with 100:1.5 methylene chloride:methanol.

B. 5,11-Dihydro-8-[[(1H-indol-3-yl)carbonyl]amino]-11-oxo-5-propyl-10H-dibenzo[b,e][1,4]-diazepine-10-acetic acid, monosodium salt Compound B was prepared from compound A as described for compound J of Example 6 (reaction heated at 40° C. for 2 hours). Example 7 was a white solid.

Melting point: greater than 240° C.

Analysis for $C_{27}H_{23}N_4O_4Na \cdot 2.7\ H_2O$ Calc'd: C 60.15; H 5.31; N 10.39 Found: C 60.33; H 4.98; N 10.29

EXAMPLE 8

5,11-Dihydro-8-[[(1H-indol-2-yl)carbonyl]amino]-11-oxo-5-propyl-10H-dibenzo[b,e][1,4]diazepine-10-acetic acid, monosodium salt

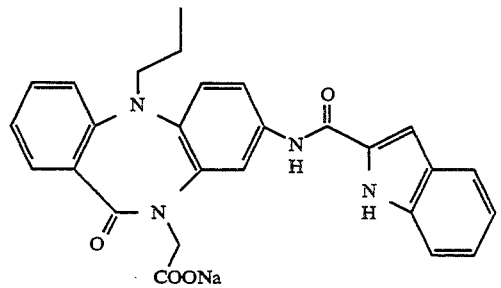

A. 5,11-Dihydro-8-[(1H-indol-2-ylcarbonyl)amino]-11-oxo-5-propyl]-10H-dibenzo[b,e][1,4]-diazepine-10-acetic acid,methyl ester.

1H-indole-3carbonyl chloride was prepared as described for 1H-indole-3-acetyl chloride of Example 6.

To a mixture of 1H-indole-3-carbonyl chloride and compound H from Example 6 (140 mg, 0.41 mmol) in 1.7 mL methylene chloride, triethylamine (146 mg, 1.44 mmol) was added. The reaction mixture was stirred for 2 hours and poured into aqueous ammonium chloride. Ether (2 mL) was added and the mixture was shaken and filtered to provide compound A as a solid.

B. 5,11-Dihydro-8-[[(1H-indol-2-yl)carbonyl]amino]-11-oxo-5-propyl-10H-dibenzo[b,e][1,4]-diazepine-10-acetic acid, monosodium salt Compound B was prepared from compound A as described for compound J of Example 6 (reaction heated at 35° C. for 2 hours). Example 8 was a white solid.

Melting point: greater than 250° C.

Analysis for $C_{27}H_{23}N_4O_4Na \cdot 2.3\ H_2O$ Calc'd: C 60.97; H 5.23; N 10.53 Found: C 61.07; H 4.97; N 10.45

EXAMPLE 9

5,11-Dihydro-8-[(1-naphthalenylmethyl)amino]-11-oxo-5-propyl-10H-dibenzo[b,e][1,4]diazepine-10-acetic acid, monosodium salt

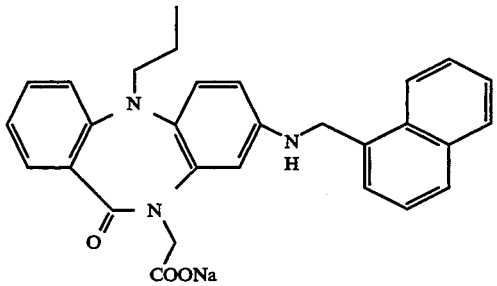

A. 5,11-Dihydro-8-[(1-naphthalenylmethyl)amino]-11-oxo-5-propyl-10H-dibenzo[b,e][1,4]-diazepine-10-acetic acid, methyl ester To a solution of compound H from Example 6 (80 mg, 0.24 mmol), 1-naphthalenecarboxaldehyde (42 mg, 0.27 mmol) and sodium acetate (19 mg, 0.24 mmol) in 2.4 mL of methanol and 0.5 mL of dichloroethane, 0.4 mL of acetic acid was added dropwise. The solution was stirred at 45° C. for 2.5 hours, cooled to room temperature and sodium cyanoborohydride (16 mg, 0.26 mmol) was added. The mixture was stirred at room temperature for 1 hour, poured into 30 mL of water, and the mixture was neutralized with sodium hydrogen carbonate and extracted with methylene chloride (3×20 mL). The organic extracts were dried (magnesium sulfate), filtered and concentrated. The residue was chromatographed on silica gel eluted with 4:1 hexanes/ethyl acetate to afford compound A as a yellow solid (100 mg, 88%). $R_f$=0.7, silica gel, 2:1 hexane/ethyl acetate.

B. 5,11-Dihydro-8-[(1-naphthalenylmethyl)amino]-11-oxo-5-propyl-10H-dibenzo[b,e][1,4]-diazepine-10-acetic acid, monosodium salt To a solution of compound A (96 mg, 0.2 mmol) in 3 mL of methanol and 3 mL of tetrahydrofuran, 1 mL of 1 N aqueous sodium hydroxide was added. The solution was heated at 40° C. for 1 hour and concentrated under vacuum, and the residue was chromatographed on an HP-20 column eluted first with water and then with 100:30 water/acetone to provide 85 mg of Example 9 as a white solid (87%).

Melting point: 190° C. (dec.).

Analysis for $C_{29}H_{26}N_3O_3Na \cdot 2.3\ H_2O$ Calc'd: C 65.85; H 5.83; N 7.94 Found: C 65.85; H 5.55; N 7.81

What is claimed is:

1. A compound of the formula

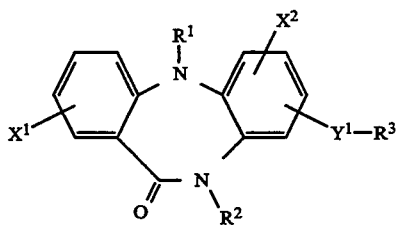

wherein:
one of $R^1$ and $R^2$ is $Y^2$-$CO_2H$ and the other is R;

R is
- (a) hydrogen,
- (b) alkyl,
- (c) alkenyl,
- (d) alkynyl,
- (e) cycloalkyl,
- (f) cycloalkenyl,
- (g) aryl,
- (h) cycloalkylalkyl,
- (i) cycloalkenylalkyl, or
- (j) aralkyl;

$R^3$ is aryl or heteroaryl;

$X^1$ and $X^2$ are each independently
- (a) hydrogen,
- (b) halo or haloalkyl,
- (c) hydroxy,
- (d) alkoxy,
- (e) cyano,
- (f) nitro, or
- (g) amino, alkylamino, or dialkylamino;

$Y^1$ is
- (a) a single bond,
- (b) alkylene,
- (c) alkenylene,
- (d) alkynylene,
- (e) $Z^1$-O-$Z^2$,
- (f) $Z^1$-C(O)-$Z^2$,
- (g) $Z^1$-O-C(O)-$Z^2$,
- (h) $Z^1$-C(O)-O-$Z^2$,
- (i) $Z^1$-N($Z^3$)-$Z^2$,
- (j) $Z^1$-C(O)-N(H)-$Z^2$,
- (k) $Z^1$-N(H)-C(O)-$Z^2$,
- (l) $Z^1$-C(S)-$Z^2$, or
- (m) $Z^1$-S-$Z^2$;

$Y^2$ is
- (a) alkylene,
- (b) alkenylene,
- (c) alkynylene,
- (d) $Z^1$-O-$Z^2$ (wherein $Z^2$ is other than a single bond),
- (e) $Z^1$-C(O)-$Z^2$,
- (f) $Z^1$-O-C(O)-$Z^2$,
- (g) $Z^1$-C(O)-O-$Z^2$ (wherein $Z^2$ is other than a single bond),
- (h) $Z^2$-C(O)-N(H)-$Z^2$ (wherein $Z^2$ is other than a single bond),
- (i) $Z^1$-N(H)-C(O)-$Z^2$,
- (j) $Z^1$-C(S)-$Z^2$, or
- (k) $Z^1$-S-$Z^2$ (wherein $Z^2$ is other than a single bond);

$Z^1$ and $Z^2$ are each independently a single bond, alkylene, alkenylene, or alkynylene; and $Z^3$ is hydrogen, lower alkyl, alkanoyl, aroyl, or aralkanoyl.

2. The compound of claim 1, wherein one of $R^1$ and $R^2$ is alkyl.

3. The compound of claim 2, wherein $R^1$ is alkyl and $R^2$ is $Y^2$-$CO_2H$.

4. The compound of claim 1, wherein $Y^2$ is alkylene, alkenylene, or alkynylene.

5. The compound of claim 2, wherein $Y^2$ is alkylene, alkenylene, or alkynylene.

6. The compound of claim 3, wherein $Y^2$ is alkylene, alkenylene, or alkynylene.

7. The compound of claim 1, wherein $Y^2$ is alkylene.

8. The compound of claim 2, wherein $Y^2$ is alkylene.

9. The compound of claim 3, wherein $Y^2$ is alkylene.

10. The compound of claim 1, wherein $R^3$ is aryl or indolyl.

11. The compound of claim 1, wherein $Y^1$ is alkylene, $Z^1$-O-$Z^2$, $Z^1$-N($Z^3$)-$Z^2$, or $Z^1$-N(H)-C(O)-$Z^2$.

12. The compound of claim 11, wherein $Z^1$ and $Z^2$ are each independently a single bond or alkylene.

13. The compound of claim 12, wherein $Z^1$ is a single bond and $Z^2$ is alkylene.

14. The compound of claim 1, wherein $R^2$ is -$Y^2$-$CO^2H$.

15. The compound of claim 1, selected from the group consisting of:

- 5,11-Dihydro-8-(1-naphthalenylmethoxy)-11-oxo-10H-dibenzo[b,e][1,4]diazepine-10-acetic acid;
- 5,11-Dihydro-8-(phenylmethoxy)-11-oxo-10H-dibenzo-[b,e][1,4]diazepine-10-acetic acid;
- 5,11-Dihydro-8-(1-naphthalenylmethoxy)-11-oxo-5-propyl-10H-dibenzo[b,e][1,4]diazepine-10-acetic acid;
- 5,11-Dihydro-8-[(1H-indol-3-yl)methyl]-11-oxo-5-propyl-10H-dibenzo[b,e][1,4]-diazepine-10-acetic acid;
- 5,11-Dihydro-8-[(1H-indol-3-yl)methyl]-11-oxo-10H-dibenzo[b,e][1,4]diazepine-10-acetic acid;
- 5,11-Dihydro-8-[[(1H-indol-3-yl)acetyl]amino]-11-oxo-5-propyl-10H-dibenzo[b,e][1,4]diazepine-10-acetic acid, monosodium salt;
- 5,11-Dihydro-8-[[(1H-indol-3-yl)carbonyl]amino]-11-oxo-5-propyl-10H-dibenzo[b,e][1,4]diazepine-10-acetic acid, monosodium salt;
- 5,11-Dihydro-8-[[(1H-indol-2-yl)carbonyl]amino]-11-oxo-5-propyl-10H-dibenzo[b,e][1,4]diazepine-10-acetic acid, monosodium salt; and
- 5,11-Dihydro-8-[(1-naphthalenylmethyl)amino]-11-oxo-5-propyl-10H-dibenzo[b,e][1,4]diazepine-10-acetic acid, monosodium salt.

16. A method of treating endothelin-related disorders in a mammal, which comprises administering an effective amount of a compound of claim 1.

* * * * *